United States Patent [19]

Lange et al.

[11] Patent Number: 5,166,179

[45] Date of Patent: * Nov. 24, 1992

[54] N-BENZOYL-N'-PHENOXYPHENYLUREAS, THEIR PREPARATION AND THEIR USE FOR CONTROLLING PESTS

[76] Inventors: Arno Lange, 3b Oberes Gaistal, 6702 Bad Durkheim; Heinrich Adolphi, 11 Kalmitweg, 6703 Limburgerhof, both of Fed. Rep. of Germany

[*] Notice: The portion of the term of this patent subsequent to Apr. 2, 2002 has been disclaimed.

[21] Appl. No.: 166,724

[22] Filed: Mar. 1, 1988

Related U.S. Application Data

[63] Continuation of Ser. No. 525,623, Aug. 23, 1983, abandoned.

[30] Foreign Application Priority Data

Aug. 31, 1982 [DE]  Fed. Rep. of Germany ....... 3232265

[51] Int. Cl.[5] ..................... C07C 275/54; A01N 47/34
[52] U.S. Cl. ........................................ 514/594; 564/44
[58] Field of Search ........................... 564/44; 514/594

[56] References Cited

U.S. PATENT DOCUMENTS

| | | |
|---|---|---|
| 4,005,223 | 1/1977 | Sirrenberg et al. ............... 564/44 X |
| 4,064,267 | 12/1977 | Sirrenberg et al. ............... 564/44 X |
| 4,123,449 | 10/1978 | Sirrenberg et al. ............... 564/44 X |
| 4,399,152 | 8/1983 | Brouwer et al. .................. 564/44 X |
| 4,508,734 | 4/1985 | Lange et al. ...................... 564/44 X |
| 4,533,676 | 8/1985 | Sirrenberg et al. .................... 564/44 |

FOREIGN PATENT DOCUMENTS

| | | |
|---|---|---|
| 44410 | 1/1982 | European Pat. Off. ............. 564/44 |
| 0057888 | 2/1982 | European Pat. Off. . |
| 74074 | 3/1983 | European Pat. Off. ............. 564/44 |
| 2531202 | 7/1975 | Fed. Rep. of Germany . |
| 3217619 | 11/1983 | Fed. Rep. of Germany ........ 564/44 |
| 0038357 | 3/1980 | Japan ..................................... 564/44 |
| 0025144 | 3/1981 | Japan ..................................... 564/44 |
| 0068659 | 6/1981 | Japan ..................................... 564/44 |
| 0092857 | 7/1981 | Japan ..................................... 564/44 |
| 0002258 | 1/1982 | Japan ..................................... 564/44 |
| 0002259 | 1/1982 | Japan ..................................... 564/44 |
| 0035163 | 3/1983 | Japan ..................................... 564/44 |
| 0039657 | 3/1983 | Japan ..................................... 564/44 |
| 0020265 | 2/1984 | Japan ..................................... 564/44 |
| 2062634 | 5/1981 | United Kingdom .................. 564/44 |

OTHER PUBLICATIONS

J. Agr. Food Chem. 21 (1973), 348.

Primary Examiner—Carolyn Elmore

[57] ABSTRACT

N-benzoyl-N'-phenoxyphenylureas of the formula (I)

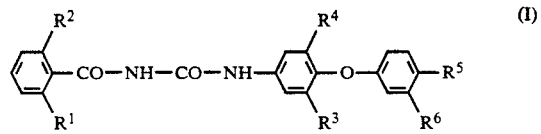

where $R^1$ is fluorine, chlorine or methyl, $R^2$ is fluorine, chlorine or hydrogen, $R^3$ and $R^4$ are each chlorine or bromine and $R^5$ and $R^6$ can be identical or different and are each fluorine, chlorine, bromine, trifluoromethyl or hydrogen, processes for their preparation and their use for controlling pests.

3 Claims, No Drawings

N-BENZOYL-N'-PHENOXYPHENYLUREAS, THEIR PREPARATION AND THEIR USE FOR CONTROLLING PESTS

This application is a continuation of application Ser. No. 525,623, filed on Aug. 23, 1983, abandoned.

It has been disclosed that N-benzoyl-N'-phenyl- or -phenoxyphenylureas can be used as insecticides (J. Agr. Food Chem. 21 (1973), 348 and German Laid-Open Application DOS 2,531,202).

We have found that N-benzoyl-N'-phenoxyphenylureas of the formula (I)

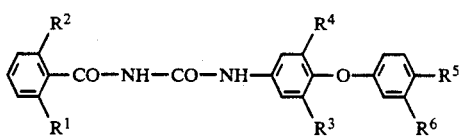

where $R^1$ is fluorine, chlorine or methyl, $R^2$ is fluorine, chlorine or hydrogen, $R^3$ and $R^4$ are each chlorine or bromine and $R^5$ and $R^6$ can be identical or different and are each fluorine, chlorine, bromine, trifluoromethyl or hydrogen, are more effective than known N-benzoyl-N'-phenoxyphenylureas in controlling pests, in particular insects.

Preferred compounds are those in which one or both of the substituents $R^5$ and $R^6$ are hydrogen, i.e. the phenoxy radical is preferably unsubstituted or monosubstituted in the 3- or 4-position.

Such N-benzoyl-N'-phenoxyphenylureas are obtained by reacting either an appropriate phenoxyaniline (II)

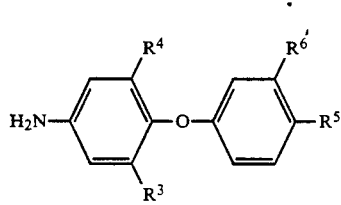

with an appropriate benzoyl isocyanate (III)

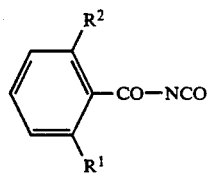

or a phenoxyphenyl isocyanate (IV)

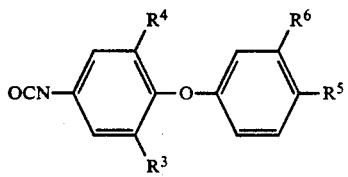

with a benzamide (V)

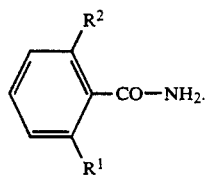

The starting materials are either known or can be readily prepared by a conventional method.

The benzoyl isocyanates (II) can be prepared, for example, by the methods described in J. Org. Chem. 28 (1963), 1805–1811 or J. Agr. Food Chem. 21 (1973), 348.

For the preparation of the phenyl isocyanates, for example, the information given in Weygand-Hilgetag, Organisch-Chemische Experimentierkunst, 1970 or in German Laid-Open Application DOS 2,538,178 is useful. The preparation of the diphenyl ethers is described, for example, by Barry et al. in Pr. Irish Acad. 53 B (1950), 61–66 and 82.

The above reactions take place under the conditions described in German Laid-Open Application DOS 2,531,202 and do not present any particular difficulties.

The novel compounds are as a rule obtained in analytically pure form; if not, they can be purified by recrystallization. They are characterized by means of elementary analysis and on the basis of their melting points and IR and NMR spectra.

The first-mentioned version of the process is advantageously carried out as follows: the substituted aniline is initially taken together with the solvent or diluent, and a stoichiometric amount of isocyanate is then added. After as a rule not more than two hours, the reaction product either has separated out as a crystalline precipitate (which is filtered off under suction) or has remained in solution. In the latter case, the solution is evaporated down under reduced pressure and the residue is dried. In the other version of the process, the reaction time is in general from more than 2 to about 6 hours, when the reaction is carried out at room temperature. A catalyst, such as triethylamine or dibutyl-tin diacetate, can be advantageous.

PREPARATION EXAMPLE a) 4.3 g of 3,5-dichloro-4-phenoxyaniline in 50 ml of toluene are initially taken, and 3.3 g of 2,6-difluorobenzoyl isocyanate are gradually added at room temperature, the temperature increasing from 22° to 32° C. Stirring is continued overnight, after which the product is filtered off under suction and dried under reduced pressure. 6.7 g of N-2,6-difluorobenzoyl-N'-(3,5-dichloro-4-phenoxyphenyl)-urea of melting point 195°–198° C. are obtained.

b) 4.3 g of 3,5-dichloro-4-(4'-chlorophenoxy)-aniline in 50 ml of toluene are initially taken, and 2.9 g of 2-chlorobenzoyl isocyanate in 5 ml of toluene are added at room temperature, the temperature increasing from 23° to 31° C. Stirring is continued overnight, after which the product is filtered off under suction and dried under reduced pressure. 6.2 g of N-2-chlorobenzoyl-N'-[3,5-dichloro-4-(4'-chlorophenoxy)-phenyl]-urea of melting point 208°–211° C. are obtained.

The compounds below were obtained by similar methods; Preparation Example a) corresponds to No. 5 and Preparation Example b) corresponds to No. 4 in the Table below.

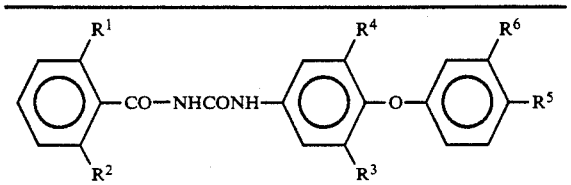

| No. | R¹ | R² | R³ | R⁴ | R⁵ | R⁶ | M.p. (°C.) |
|-----|----|----|----|----|----|----|------------|
| 1 | F | F | Cl | Cl | Cl | H | 199-202 |
| 2 | Cl | Cl | Cl | Cl | Cl | H | 229-232 |
| 3 | Cl | F | Cl | Cl | Cl | H |  |
| 4 | Cl | H | Cl | Cl | Cl | H | 208-211 |
| 5 | F | F | Cl | Cl | H | H | 195-198 |
| 6 | Cl | Cl | Cl | Cl | H | H | 216-219 |
| 7 | Cl | H | Cl | Cl | H | H | 208-212 |
| 8 | F | F | Cl | Cl | F | H | 201-203 |
| 9 | Cl | Cl | Cl | Cl | F | H | 211-214 |
| 10 | Cl | H | Cl | Cl | F | H | 174-178 |
| 11 | F | F | Cl | Cl | Br | H | 210-215 |
| 12 | Cl | Cl | Cl | Cl | Br | H | 230-234 |
| 13 | Cl | H | Cl | Cl | Br | H | 217-220 |
| 14 | F | F | Cl | Cl | CF₃ | H | 192-195 |
| 15 | Cl | Cl | Cl | Cl | CF₃ | H | 180-185 |
| 16 | Cl | H | Cl | Cl | CF₃ | H | 212-218 |
| 17 | F | F | Cl | Cl | H | Cl | 192-194 |
| 18 | Cl | Cl | Cl | Cl | H | Cl | 204-210 |
| 19 | Cl | H | Cl | Cl | H | Cl | 198-205 |
| 20 | F | F | Cl | Cl | H | CF₃ | 170-174 |
| 21 | Cl | Cl | Cl | Cl | H | CF₃ | 189-195 |
| 22 | Cl | H | Cl | Cl | H | CF₃ | 187-190 |
| 23 | F | F | Br | Cl | H | H | 175-178 |
| 24 | Cl | Cl | Br | Cl | H | H | 205-209 |
| 25 | Cl | H | Br | Cl | H | H | 205-210 |
| 26 | F | F | Br | Cl | Cl | H | 205-208 |
| 27 | Cl | Cl | Br | Cl | Cl | H | 245-249 |
| 28 | Cl | H | Br | Cl | Cl | H | 210-214 |
| 29 | F | F | Br | Br | H | H | 178-185 |
| 30 | Cl | Cl | Br | Br | H | H | 225-228 |
| 31 | Cl | H | Br | Br | H | H | 220-224 |
| 32 | F | F | Br | Br | Cl | H | 206-210 |
| 33 | Cl | Cl | Br | Br | Cl | H | 244-248 |
| 34 | Cl | H | Br | Br | Cl | H | 212-218 |

The N-benzoyl-N'-phenoxyphenylureas of the formula I are suitable for effectively combating pests particularly from the insect class. They mey be used as pesticides for protecting crops, and in the hygiene, stores protection and veterinary sectors. A particularly important area of use for the agents according to the invention is the control of caterpillars of harmful butterflies.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarius, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar., Lymantria monacha, Pieris brassicae,* and *Aporia crataegi;* examples from the Coleoptera order are *Blitophaga undata, Melanotus communis, Limonius californicus, Agriotes lineatus, Agricotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Lycoria pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ovis, Chrysomya macellaria, Chrysomya hominivorax, Lucilia cuprina, Lucilia sericata,* and *Hypoderma lineata;* examples from the Hymenoptera order are *Athalia rosae, Hoplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysaphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* examples from the Isoptera order are *Reticulitermes lucifugus, Calotermes flavicollis, Leucotermes flavipes,* and *Termes natalensis;* examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blattella germanica, Periplaneta americana,* and *Blabera gigantea.*

Examples of mites and ticks (Acarina) belonging to the Arachnida class are *Tetranychus telarius, Tetranychus atlanticus, Tetranychus pacificus, Paratetranychus pilosus, Bryobia praetiosa, Ixodes ricinus, Ornithodorus moubata, Ablyomma americanum, Dermacentor silvarum,* and *Boophilus microplus.*

Examples from the Nemathelminthes class are root-knot nematodes, e.g., *Meloidogyne incognita, Meloidogyne hapla,* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Pratylen-*

*chus curvitatus* and *Tylenchorhynchus dubius, Tylenchorhynchus claytoni, Rotylenchus robustus, Heliocotylenchus multicinctus, Radopholus similis, Belonolaimus longicaudatus, Longidorus elongatus,* and *Trichodorus primitivus.*

The active ingredients may be applied as such, as formulations, or application forms prepared therefrom, e.g., in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are as follows:

I. 5 parts by weight of compound no. 1 is intimately mixed with 95 parts by weight of particulate kaolin. A dust is obtained containing 5% by weight of the active ingredient.

II. 30 parts by weight of compound no. 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 4 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

IV. 20 parts by weight of compound no. 13 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

V. 80 parts by weight of compound no. 19 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90, % by weight of active ingredient.

The amount of active ingredient in the ready-to-use formulations may vary within a wide range; it is generally from 0.0001 to 10%, preferably from 0.01 to 1%.

The active ingredients may also be successfully used in the ultra-low volume method, where it is possible to apply formulations containing more than 95 wt. % of active ingredient, or even the 100% active ingredient.

In the open, application rates are from 0.2 to 10, and preferably from 0.5 to 2.0, kg of active ingredient per hectare.

There may be added to the individual active ingredients (if desired, immediately before use (tankmix)) oils of various types, herbicides, fungicides, other pesticides and bactericides. These agents may be added to the active ingredients according to the invention in a weight ratio of from 1:10 to 10:1.

Examples of active ingredients which may be admixed are as follows: 1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenyl-phosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorodithioate, O,O-dimethyl-S-(N-methoxyethylcarbamoyl-methyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]9 -phosphorodithioate, O,O-dimethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl(3)]-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-dimethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazine-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, alpha-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl(±)-cis,trans-2,2-dimethyl-3-(2,2-dichlorovinyl)-cyclopropanecarboxylate, alpha-cyano-3-phenoxybenzyl(±)-cis,trans-2,2-dimethyl-3-(2,2-dichlorovinyl)-cyclopropane carboxylate, (s)-alpha-cyano-3-phenoxybenzyl-cis(1R,3R)-2,2-dibromovinyl)-cyclopropane carboxylate, 3,4,5,6-tetrahydrophthalimidoethyl-DL-cis,trans-chrysanthemate, 2-methyl-5-(2-propynyl)-3-furylmethyl-chrysanthemate, and alpha-cyano-3-phenoxybenzyl-alpha-isopropyl-4-chlorophenylacetate.

As the examples which follow show, the N-benzoyl-N'-phenoxyphenylureas have an action which in many species is much better than, and in most species is at least as good as, that of comparable prior art agents; for comparison purposes in the use examples below, the commercial product Diflubenzuron of the formula

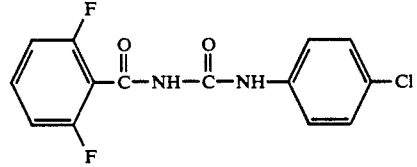

was selected.

USE EXAMPLE 1

Breeding experiment with mosquito larvae (*Aedes aegypti*)

30 to 40 larvae of *Aedes aegypti* in the 4th larval stage were introduced into 200 ml of tap water to which the active ingredient formulation had been added.

The temperature at which the experiment was carried out was 25° C. Pupation and hatching of the adults were assessed, an untreated control being used for reference. During the experiment, a conventional pulverized food for aquarium fish was fed once.

Compounds nos. 1, 2, 4, 5 and 8, at concentrations of 0.001 to 0.04 ppm, had an absolutely lethal action. Under comparable conditions the comparative agent had a similar action—some compounds according to the invention are clearly superior.

USE EXAMPLE 2

Breeding experiment with corn borer larvae (*Ostrinia nubilalis*)

515 g cornflour
130 g wheat germ
137 g brewer's yeast
18 g ascorbic acid
10 g cellulose powder
5 g Nipagin
20 g Wessons salt
20 ml vitamin solution
80 g agar
3,100 ml water.

50 ml of this medium was filled into 100 ml plastic beakers, and aqueous active ingredient formulations were carefully mixed in. When the vessels were cold, 4 caterpillars (L3) were introduced into each. For each concentration, 5 vessels were used.

Monitoring was carried out until the moths emerged.

In this experiment, compounds nos. 1, 2 and 4 achieved 100% mortality at concentrations of from 0.4 to 4.0 ppm, and agent no. 5 had 92% mortality at 1.0 ppm. By contrast, the action of the comparative agent was still not lethal at 5.0 ppm.

USE EXAMPLE 3

Breeding experiment with cotton stainers (*Dysdercus intermedius*)

Cotton stainers (*Dysdercus intermedius*) in the 4th larval stage were exposed to a layer of the candidate compounds in Petri dishes 10 cm in diameter.

The survivors were then kept in 1 liter jars on moist quartz sand (to which active ingredient solutions had been added) until the $F_1$ generation hatched.

In the treatment, 2.5 mg/dish was equivalent to 25 ppm in the sand;
1.0 mg/dish was equivalent to 10 ppm in the sand;
0.5 mg/dish was equivalent to 5 ppm in the sand; etc.

Mortality and multiplication were assessed.

In this test, compounds nos. 1 and 4 revealed themselves to be twice to 5 times more effective than the comparative agent.

USE EXAMPLE 4

Breeding experiment with houseflies (*Musca domestica*)

4.5 ml of skimmed milk was introduced into 50 ml penicillin flasks, and 0.5 ml of the aqueous active ingredient formulation was then added. After brief mixing, a ball of absorbent cotton was introduced and about 50 housefly larvae placed on it. The flasks were covered and kept at room temperature. The development was assessed after 7 days.

In this test, compounds nos. 1, 4 and 5 had an absolutely lethal action at concentrations of from 5 to 20 ppm.

We claim:

1. An N-benzoyl-N'-phenoxy-phenylurea of the formula

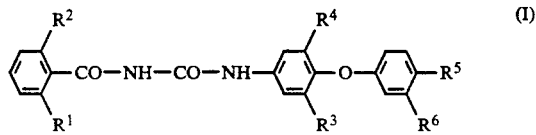

where $R^1$ is fluorine, $R^2$ is fluorine, $R^3$ and $R^4$ are each chlorine, $R^5$ is chlorine and $R^6$ is hydrogen.

2. An agent for combating insects which comprises: a solid or liquid carrier and an effective amount of an N-benzoyl-N'-phenoxyphenylurea of the formula I as defined in claim 1.

3. A process for combating pests, wherein an effective amount of an N-benzoyl-N'-phenoxyphenylurea of the formula I as defined in claim 1 is allowed to act on the pests and/or their habitat.

* * * * *